(12) United States Patent
Idiris et al.

(10) Patent No.: US 10,465,199 B2
(45) Date of Patent: Nov. 5, 2019

(54) TRANSFORMANT, AND METHOD FOR PRODUCING TRANSFERRIN

(71) Applicant: AGC Inc., Chiyoda-ku (JP)

(72) Inventors: Alimjan Idiris, Chiyoda-ku (JP); Hiromichi Kumagai, Chiyoda-ku (JP); Chiaki Kojima, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/033,832

(22) Filed: Jul. 12, 2018

(65) Prior Publication Data

US 2018/0312853 A1     Nov. 1, 2018

Related U.S. Application Data

(63) Continuation of application No. PCT/JP2017/000497, filed on Jan. 10, 2017.

(30) Foreign Application Priority Data

Jan. 12, 2016    (JP) ................. 2016-003606

(51) Int. Cl.
| | |
|---|---|
| C12P 21/00 | (2006.01) |
| C12N 15/09 | (2006.01) |
| C07K 14/79 | (2006.01) |
| C12N 15/64 | (2006.01) |
| C12P 21/02 | (2006.01) |
| C12N 15/81 | (2006.01) |

(52) U.S. Cl.
CPC ............ *C12N 15/815* (2013.01); *C07K 14/79* (2013.01); *C12N 15/09* (2013.01); *C12N 15/64* (2013.01); *C12P 21/00* (2013.01); *C12N 2510/02* (2013.01); *C12P 21/02* (2013.01)

(58) Field of Classification Search
None
See application file for complete search history.

(56) References Cited

U.S. PATENT DOCUMENTS

| 8,329,448 | B2 | 12/2012 | Idiris et al. |
| 2013/0122547 | A1 | 5/2013 | Idiris et al. |
| 2014/0335622 | A1 | 11/2014 | Kotani et al. |

FOREIGN PATENT DOCUMENTS

| JP | 2011-125281 A | | 6/2011 |
| JP | 2011125281 A | * | 6/2011 |
| WO | 2007/015470 A1 | | 2/2007 |
| WO | 2013/111754 A1 | | 8/2013 |

OTHER PUBLICATIONS

Ferrer et al. (1998) Yeast Cell Permeabilizing β-1,3-Glucanases: A Tool for the Integration of Downstream Processes and Metabolic Engineering Applications. Biotechnology and Bioengineering, 58:321-324 (Year: 1998).*
Medina-Redondo et al. (2010) β(1,3)-Glucanosyl-Transferase Activity Is Essential for Cell Wall Integrity and Viability of Schizosaccharomyces pombe. PLoS One, 5(11):e14046, pp. 1-13 (Year: 2010).*
Mattanovich et al. "Recombinant Protein Production in Yeasts" in: Recombinant Gene Expression: Reviews and Protocols, Third Edition, Methods in Molecular Biology, (2012) vol. 824, pp. 329-358 (Year: 2012).*
English Machine Translation for JP-2011125281 (Year: 2011).*
De Medina-Redondo et al.—β(1.3)-Glucanosyl-Transferase Activity is Essential for Cell Wall Integrity and Viability of Scyzosaccharomyces pombe, PLoS One, 2010, vol. 5, e14046 (13 pages).
International Search Report dated Apr. 4, 2017 issued in PCT/JP2017/000497 (with English translation).

* cited by examiner

*Primary Examiner* — Neil P Hammell
(74) *Attorney, Agent, or Firm* — Oblon, McClelland, Maier & Neustadt, L.L.P.

(57) ABSTRACT

To provide a method for producing transferrin by secretion with high productivity using a transformant of *Schizosaccharomyces pombe*, and a transformant suitable for the method.

A transformant using *Schizosaccharomyces pombe* as a host, comprising a transferrin gene and a secretion signal peptide gene expressing transferrin to which a secretion signal peptide which functions in the host binds, located in an upstream region of the transferrin gene, and having gas2 gene endogenous to the host deleted or inactivated; and a method for producing transferrin, which comprises culturing the transformant in a liquid medium and obtaining transferrin from the liquid medium.

16 Claims, 2 Drawing Sheets

Specification includes a Sequence Listing.

SEQUENCE LISTING

<160> NUMBER OF SEQ ID NOS: 25

<210> SEQ ID NO 1
<211> LENGTH: 2097
<212> TYPE: DNA
<213> ORGANISM: Homo sapiens

<400> SEQUENCE: 1

```
atgaggctcg ccgtgggagc cctgctggtc tgcgccgtcc tggggctgtg tctggctgtc      60
cctgataaaa ctgtgagatg gtgtgcagtg tcggagcatg aggccactaa gtgccagagt     120
ttccgcgacc atatgaaaag cgtcattcca tccgatggtc ccagtgttgc ttgtgtgaag     180
aaagcctcct accttgattg catcagggcc attgcggcaa acgaagcgga tgctgtgaca     240
ctggatgcag gtttggtgta tgatgcttac ctggctccca taacctgaa gcctgtggtg      300 gcagagttct atgggtcaaa agaggatcca cagactttct attatgctgt tgctgtggtg     360
aagaaggata gtggcttcca gatgaaccag cttcgaggca gaagtcctg ccacacgggt      420 ctaggcaggt ccgctgggtg gaacatcccc ataggcttac tttactgtga cttacctgag     480
ccacgtaaac ctcttgagaa agcagtggcc aatttcttct cgggcagctg tgccccttgt     540
gcggatggga cggacttccc ccagctgtgt caactgtgtc cagggtgtgg ctgctccacc     600
cttaaccaat acttcggcta ctcaggagcc ttcaagtgtc tgaaggatgg tgctggggat     660
gtggcctttg tcaagcactc gactatattt gagaacttgg caaacaaggc tgacagggac     720
cagtatgagc tgctttgcct ggacaacacc cggaagccgg tagatgaata caaggactgc     780
cacttggccc aggtcccttc tcataccgtc gtggcccgaa gtatgggcgg caaggaggac     840
ttgatctggg agcttctcaa ccaggcccag gaacattttg gcaaagacaa atcaaaagaa     900
ttccaactat tcagctctcc tcatgggaag gacctgctgt ttaaggactc tgcccacggg     960
tttttaaaag tcccccccag gatggatgcc aagatgtacc tgggctatga gtatgtcact    1020
gccatccgga atctacggga aggcacatgc ccagaagccc aacagatga atgcaagcct    1080 gtgaagtggt gtgcgctgag ccaccacgag aggctcaagt gtgatgagtg gagtgttaac    1140
agtgtaggga aaatagagtg tgtatcagca gagaccaccg aagactgcat cgccaagatc    1200
atgaatggag aagctgatgc catgagcttg gatggagggt ttgtctacat agcgggcaag    1260
tgtggtctgg tgcctgtctt ggcagaaaac tacaataaga gcgataattg tgaggataca    1320
ccagaggcag ggtattttgc tgtagcagtg gtgaagaat cagcttctga cctcacctgg     1380
gacaatctga aaggcaagaa gtcctgccat acggcagttg gcagaaccgc tggctggaac    1440
atccccatgg gcctgctcta caataagatc aaccactgca gatttgatga atttttcagt    1500
gaaggttgtg ccctgggtc taagaaagac tccagtctct gtaagctgtg tatgggctca    1560
ggcctaaacc tgtgtgaacc caacaacaaa gagggatact acggctacac aggcgctttc    1620
aggtgtctgg ttgagaaggg agatgtggcc tttgtgaaac accagactgt cccacagaac    1680
```

```
actgggggaa aaaaccctga tccatgggct aagaatctga atgaaaaaga ctatgagttg    1740
ctgtgccttg atggtaccag gaaacctgtg gaggagtatg cgaactgcca cctggccaga    1800
gccccgaatc acgctgtggt cacacggaaa gataaggaag cttgcgtcca caagatatta    1860
cgtcaacagc agcacctatt tggaagcaac gtaactgact gctcgggcaa cttttgtttg    1920
ttccggtcgg aaaccaagga ccttctgttc agagatgaca cagtatgttt ggccaaactt    1980
catgacagaa acacatatga aaaatactta ggagaagaat atgtcaaggc tgttggtaac    2040
ctgagaaaat gctccacctc atcactcctg gaagcctgca cttccgtag accttaa      2097
```

```
<210> SEQ ID NO 2
<211> LENGTH: 2040
<212> TYPE: DNA
<213> ORGANISM: Homo sapiens

<400> SEQUENCE: 2
```

```
gtccctgata aaactgtgag atggtgtgca gtgtcggagc atgaggccac taagtgccag      60
agtttccgcg accatatgaa aagcgtcatt ccatccgatg gtcccagtgt tgcttgtgtg     120
aagaaagcct cctaccttga ttgcatcagg gccattgcgg caaacgaagc ggatgctgtg     180
acactggatg caggtttggt gtatgatgct tacctggctc ccaataacct gaagcctgtg     240
gtggcagagt tctatgggtc aaaagaggat ccacagactt tctattatgc tgttgctgtg     300
gtgaagaagg atagtggctt ccagatgaac cagcttcgag gcaagaagtc ctgccacacg     360
ggtctaggca ggtccgctgg gtggaacatc cccataggct tactttactg tgacttacct     420
gagccacgta acctcttga gaaagcagtg gccaatttct tctcgggcag ctgtgcccct     480
tgtgcggatg ggacggactt cccccagctg tgtcaactgt gtccagggtg tggctgctcc     540
acccttaacc aatacttcgg ctactcagga gccttcaagt gtctgaagga tggtgctggg     600
gatgtggcct ttgtcaagca ctcgactata tttgagaact ggcaaacaa ggctgacagg     660 gaccagtatg agctgctttg cctggacaac acccggaagc cggtagatga atacaaggac     720
tgccacttgg cccaggtccc ttctcatacc gtcgtggccc gaagtatggg cggcaaggag     780
gacttgatct gggagcttct caaccaggcc caggaacatt ttggcaaaga caaatcaaaa     840
gaattccaac tattcagctc tcctcatggg aaggacctgc tgtttaagga ctctgcccac     900 gggttttaa aagtcccccc caggatggat gccaagatgt acctgggcta tgagtatgtc     960
actgccatcc ggaatctacg ggaaggcaca tgcccagaag ccccaacaga tgaatgcaag    1020
cctgtgaagt ggtgtgcgct gagccaccac gagaggctca gtgtgatga gtggagtgtt    1080 aacagtgtag ggaaaatag gtgtgtatca gcagagacca ccgaagactg catcgccaag    1140
atcatgaatg gagaagctga tgccatgagc ttggatggag gtttgtcta catagcgggc    1200 aagtgtggtc tggtgcctgt cttggcagaa aactaccaaa agagcgataa ttgtgaggat    1260
acaccagagg cagggtattt tgctgtagca gtggtgaaga atcagcttc tgacctcacc    1320 tgggacaatc tgaaaggcaa gaagtcctgc catacggcag ttgcagaac cgctggctgg    1380 aacatccccca tgggcctgct ctacaataag atcaaccact gcagatttga tgaattttc    1440 agtgaaggtt gtgcccctgg gtctaagaaa gactccagtc tctgtaagct gtgtatgggc    1500
tcaggcctaa acctgtgtga acccaacaac aaagagggat actacggcta cacaggcgct    1560
ttcaggtgtc tggttgagaa gggagatgtg gcctttgtga acaccagac tgtcccacag    1620 aacactgggg gaaaaaccc tgatccatgg gctaagaatc tgaatgaaaa agactatgag    1680
```

```
ttgctgtgcc ttgatggtac caggaaacct gtggaggagt atgcgaactg ccacctggcc    1740
agagccccga atcacgctgt ggtcacacgg aaagataagg aagcttgcgt ccacaagata    1800
ttacgtcaac agcagcacct atttggaagc caagtaactg actgctcggg caacttttgt    1860
ttgttccggt cggaaaccaa ggaccttctg ttcagagatg acacagtatg tttggccaaa    1920
cttcatgaca gaaacacata tgaaaaatac ttaggagaag aatatgtcaa ggctgttggt    1980
aacctgagaa aatgctccac ctcatcactc ctggaagcct gcactttccg tagaccttaa    2040
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Forward
      primer #9220

<400> SEQUENCE: 3
gagacttaag aagcgtgtcc ctgataaaac tgtgagatgg    40

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Reverse
      primer #9221

<400> SEQUENCE: 4
ctcttctaga ttaaggtcta cggaaagtgc    30

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Forward
      primer #6164

<400> SEQUENCE: 5
gcaagtactg ctcttgatct g    21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Reverse
      primer #6167

<400> SEQUENCE: 6
taaagcatcc actttgagca a    21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Forward
      primer #6153

<400> SEQUENCE: 7
tctgttggca acatgtctc    19

<210> SEQ ID NO 8

```
<211> LENGTH: 25
<212> TYPE: DNA
<213> ORGANISM: Artificial Sequence
<220> FEATURE:
<223> OTHER INFORMATION: Description of Artificial Sequence: Reverse
      primer #6156

<400> SEQUENCE: 8
gtgaaagtag attatccatg aggtc                                         25

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Forward
      primer #7243

<400> SEQUENCE: 9
tgccttttac ggttctttgg tc                                            22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Reverse
      primer #7246

<400> SEQUENCE: 10
tgcacatcag gtagcccgac                                               20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Forward
      primer #7255

<400> SEQUENCE: 11
tcattaagtc gtcgtcaaac gg                                            22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Reverse
      primer #7258

<400> SEQUENCE: 12
ctttaggtcg tcaatttcgt gc                                            22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Forward
      primer #6917

<400> SEQUENCE: 13
catactcccc tgatgtttcg c                                             21

<210> SEQ ID NO 14
<211> LENGTH: 24
```

```
<212> TYPE: DNA
<213> ORGANISM: Artificial Sequence
<220> FEATURE:
<223> OTHER INFORMATION: Description of Artificial Sequence: Reverse
      primer #6920

<400> SEQUENCE: 14
cattcatggt ggtaagagtg ttcc                                        24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Forward
      primer #9515

<400> SEQUENCE: 15
accaatcttc catatcccct tg                                          22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Reverse
      primer #9518

<400> SEQUENCE: 16
gctacgaaag cttcaactgc g                                           21

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Forward
      primer #9883

<400> SEQUENCE: 17
aaagttcttt gttttcaatt tccatg                                      26

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Reverse
      primer #9886

<400> SEQUENCE: 18
tccttataaa cgagctatcg aattg                                       25

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Forward
      primer #6175

<400> SEQUENCE: 19
gaatcatact acgatcagtt gc                                          22

<210> SEQ ID NO 20
<211> LENGTH: 23
<212> TYPE: DNA
```

```
<213> ORGANISM: Artificial Sequence
<220> FEATURE:
<223> OTHER INFORMATION: Description of Artificial Sequence: Reverse
      primer #6178

<400> SEQUENCE: 20
gaaatttact cacagggaag aac                                              23

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Forward
      primer #10493

<400> SEQUENCE: 21
gaatgtccat ataagtcaat gatgagc                                          27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Reverse
      primer #10496

<400> SEQUENCE: 22
gaggttaacg actatggtct tgttaac                                          27

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: ER
      retention signal

<400> SEQUENCE: 23

Ala Asp Glu Leu
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: active site
      for molecular chaperone activity

<400> SEQUENCE: 24

Cys Gly His Cys
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 25

Leu Lys Lys Arg
1
```

TRANSFORMANT, AND METHOD FOR PRODUCING TRANSFERRIN

This application is a continuation of PCT Application No. PCT/JP2017/000497 filed on Jan. 10, 2017, which is based upon and claims the benefit of priority from Japanese Patent Application No. 2016-003606 filed on Jan. 12, 2016. The contents of those applications are incorporated herein by reference in their entireties.

TECHNICAL FIELD

The present invention relates to a method for producing transferrin by using a transformant from *Schizosaccharomyces pombe* (hereinafter referred to as "*S. pombe*") as a host and having a transferrin gene integrated thereinto.

BACKGROUND ART

Transferrin (hereinafter sometimes referred to as "TF") is one of glycoproteins which bind to $Fe^{3+}$ ions and is deeply involved in iron metabolism. Particularly human serum transferrin (hereinafter sometimes referred to as "human transferrin" or "hTF") belongs to a family of iron-binding proteins in a human body, is involved in iron transport/metabolism in the body and is used as additives to be used for a medium for animal cell culture, a pharmaceutical preparation or a DDS carrier. TF is an about 80 kDa glycoprotein having two domains named N-lobe and C-lobe, and it is synthesized by translation as an immature protein having a secretion signal peptide at its N-terminal and is then secreted out of the cell as a mature glycoprotein having the secretion signal peptide cleaved.

As the most common method for TF production, a method for producing a full-length recombinant protein by using a cell line of mammal cells such as baby hamster kidney cells (BHK cells) has been known. Further, a method of using budding yeast *S. pombe* has been known. *S. pombe* has, as different from budding yeast *Saccharomyces cerevisiae*, cell division and transcription forms close to those of human cells and contains no substance which has adverse effects on the body. Accordingly, the method for producing TF full-length recombinant protein employing *S. pombe* is excellent as a method for producing TF to be administered to human, such as a pharmaceutical preparation. For example, Patent Document 1 discloses a method such that a transformant using *S. pombe* as a host and having a hTF gene introduced is cultured in a liquid medium containing casamino acids to efficiently produce hTF, which is made to be secreted to the liquid medium and recovered.

On the other hand, in a heterologous protein production system employing an eukaryotic microorganism such as a yeast, in order to improve the efficiency for production of the desired heterologous protein, it has been known to use an improved host having a part of or the entire genome portion of a host unnecessary or disadvantageous for heterologous protein production eliminated or inactivated. For example, Patent Document 2 discloses that use of an improved host having at least one gene selected from genes encoding a specific protease (protease gene group) of *S. pombe* eliminated or inactivated, improves the efficiency for production of a heterologous protein.

Further, hTF protein can be secreted and produced by production in a state where a secretion signal (endoplasmic reticulum targeting signal) peptide is added to the N-terminal of hTF protein. For example, by culturing a transformant of *S. pombe* which has introduced a structural gene encoding a fusion protein having a secretion signal peptide recognized by *S. pombe*, such as a polypeptide derived from secretion signal of a precursor of a mating pheromone (P-factor) relating to mating of *S. pombe*, fused to the N-terminal of hTF protein, from the produced fusion protein, secretion signal peptide is removed in the Golgi apparatus or the endoplasmic reticulum, and hTF protein is secreted into the medium. For example, Patent Document 3 discloses that by expressing, at the N-terminal side of the desired foreign protein, a partial protein composed of a secretion signal peptide of PDI1 (protein disulfide isomerase 1) which is a protein having a molecular chaperone function and localized in the endoplasmic reticulum, an a-domain, a b-domain and an x-domain, or a partial protein composed of an endoplasmic reticulum targeting signal peptide of PDI1, an a-domain, a b-domain, a b'-domain and an x-domain, in a fused state, the amount of secretory production of the foreign protein by *S. pombe* can be increased. PDI1 comprises, from the N-terminal, an ER targeting signal, a-domain, b-domain, b'-domain, x-domain, a'-domain and c-domain containing an ER retention signal (ADEL) (SEQ ID NO: 23), in this order. Each of the a-domain and the a'-domain has one active site (CGHC) (SEQ ID NO: 24) for molecular chaperone activity. All the four domains a, b, b' and a' form a thioredoxin fold.

PRIOR ART DOCUMENTS

Patent Documents

Patent Document 1: JP-A-2011-125281
Patent Document 2: WO2007/015470
Patent Document 3: WO2013/111754

DISCLOSURE OF INVENTION

Technical Field

The object of the present invention is to provide a method for producing TF by secretion with high productivity using a transformant of *S. pombe*, and a transformant suitable for the method.

Solution to Problem

The transformant of the present invention is a transformant using *S. pombe* as a host, comprising a TF gene and a secretion signal peptide gene expressing TF to which a secretion signal peptide which functions in the host binds, located in an upstream region of the TF gene, and having gas2 gene endogenous to the host deleted or inactivated.

The transformant is preferably such that the TF gene is a gene encoding human transferrin.

Further, the transformant is preferably such that the TF gene is a mutant TF gene having a mutation introduced to a gene encoding natural mammal TF, and the mutant TF gene is a gene encoding mutant TF having at least one aspartic residue which is an N-linked glycosylated portion of natural TF deleted or substituted with another amino acid residue.

Further, the transformant is preferably such that at least one protease gene endogenous to the host is deleted or inactivated. The protease gene is preferably a gene selected from the group consisting of a metalloproteinase gene group, a serine protease gene group, a cysteine protease gene group and an aspartic protease gene group. The protease gene to be deleted or inactivated is preferably at least one gene selected from the group consisting of psp3 gene, isp6 gene, ppp53 gene, ppp16 gene, ppp22 gene, sxa2 gene, ppp80 gene and ppp20 gene.

The transformant is preferably such that the TF gene is located downstream of a gene encoding a secretory carrier protein containing a secretion signal peptide, directly or indirectly, and more preferably such that the gene encoding a secretory carrier protein is a fusion gene of a gene encoding a secretion signal peptide portion of host PDI1, a gene encoding an ab-domain portion of human PDI1, and a gene encoding an x-domain portion of host PDI1.

The method for producing TF of the present invention comprises culturing the transformant of the present invention in a liquid medium and obtaining transferrin from the liquid medium.

The method for producing TF is preferably such that the transformant is cultured in a liquid medium having a pH of from 5.5 to 6.5, preferably such that the transformant is cultured in a liquid medium containing adenine, and also preferably such that the transformant is cultured until the cell-density ($OD_{660}$) reaches 100 or higher, and then transferrin is obtained from the liquid medium.

The method for producing a transformant of the present invention comprises integrating into S. pombe as a host, a secretion signal peptide gene which functions in the host, and a TF gene located downstream of the secretion signal peptide gene, and deleting or inactivating gas2 gene endogenous to the host.

Advantageous Effects of Invention

By culturing the transformant of the present invention, TF can be produced efficiently.

Further, according to the method for producing TF of the present invention, TF can be produced by secretion with high productivity using S. pombe.

DESCRIPTION OF EMBODIMENTS

[TF Gene, Secretion Signal Peptide Gene]

In the present invention, "TF gene" means a structural gene encoding mature TF protein. Further, the mature TF protein will be hereinafter referred to as "TF protein".

In cells of a species to which the TF gene is endogenous, a fusion protein having a protein (secretory carrier protein) containing a secretion signal peptide and TF protein linked to each other, is expressed, and from the fusion protein, the secretory carrier protein is cleaved out in the endoplasmic reticulum or the Golgi apparatus, and the TF protein is secreted out of the cells.

On the other hand, since TF gene is exogenous to S. pombe as a host in the present invention, even when a fusion protein having a secretory carrier protein and TF protein linked to each other is expressed in the host, the secretory carrier protein is not necessarily cleaved out in the hot cells. Accordingly, as the secretion signal peptide or the secretory carrier protein in the present invention is preferably a secretion signal peptide or a secretory carrier protein other than one endogenous to the host at its N-terminal side of TF protein, which sufficiently functions in the host. In the present invention, the term (a secretion signal peptide which) "functions in the host" means having a function to secrete the fusion protein expressed in the host out of the host cells as the TF protein.

Further, in the present invention, the TF protein and the secretion signal peptide or the secretory carrier protein may be directly linked to each other, or may be indirectly linked to each other by a linker composed of a peptide comprising one to several tens amino acid residues.

[Transformant]

The transformant of the present invention is a transformant using S. pombe as a host, comprising a TF gene and a secretion signal peptide gene expressing TF protein to which a secretion signal peptide which functions in the host binds, located in an upstream region of the TF gene, and having gas2 gene endogenous to the host deleted or inactivated.

The TF protein encoded by the TF gene which the transformant of the present invention has, may be a natural TF protein derived from any species (TF protein encoded by a TF gene present in the chromosome of a wild type organism) or may be a modified protein of a natural IF protein. The modified protein may, for example, be a polypeptide comprising an amino acid sequence of a natural TF protein, in which one or several amino acids are substituted, added or deleted, and having a TF function. A polypeptide comprising an amino acid sequence having an identity to the amino acid sequence of a natural TF protein of at least 80%, preferably at least 85%, more preferably at least 90%, further preferably at least 95%, and having a TF function, may be mentioned. The TF function means a function to bind to $Fe^{3+}$ ions and to bind to the TF receptor on the cell surface to be incorporated into the cell. The TF protein encoded by the TF gene which the transformant of the present invention has, is preferably a natural TF protein derived from a mammal such as human, monkey, mouse, rat, rabbit, cattle, horse, dog, cat, etc., or a modified protein thereof, particularly preferably hTF or a modified protein thereof.

In a case where the TF protein encoded by the TF gene which the transformant of the present invention has, is a modified protein of a natural TF protein, the modification is, for example, preferably point mutation such that at least one aspartic acid residue as the N-linked glycosylated portion after translation, is deleted or substituted by another amino acid residue. In a case where a protein having a N-linked glycosylated portion is produced by secretion, the resulting recombinant protein is modified with a high mannose sugar chain having non-uniform length, and the uniformity or the quality may thereby be decreased.

In a case where the TF gene which the transformant of the present invention has, is a modified TF gene encoding a modified TF protein mutated to delete the N-linked glycosylated portion, by culturing such a transformant, a recombinant TF protein which has a stable TF function and which has a uniform quality can be produced by secretion. For example, such a modified TF gene is preferably a modified TF gene encoding a modified TF protein in which at least one aspartic acid residue as an N-linked glycosylated portion of the two N-linked glycosylated portions (432nd and 630th aspartic acid residues) of a natural hTF protein, is deleted or substituted with an amino acid residue other than an aspartic acid residue, more preferably a modified TF gene encoding a modified TF protein in which the two N-linked glycosylated portions are substituted with an amino acid residue other than an aspartic acid residue, further preferably a modified TF gene (SEQ ID NO: 2) encoding a mutant TF protein in which the two N-linked glycosylated portions are substituted with glutamine residue.

The secretion signal peptide gene which the transformant of the present invention has is a structural gene encoding a secretion signal peptide which functions in the transformant cell. The secretion signal peptide gene may be a part of a structural gene encoding a secretory carrier protein. That is, the structural gene encoding a secretory carrier protein may have a structural gene portion encoding a secretory carrier protein other than the secretion signal peptide gene portion, downstream the secretion signal peptide gene. The secretion signal peptide may be any peptide which functions in S. pombe and may, for example, be ones disclosed in WO1996/123890 such as a secretion signal peptide of a secretory protein endogenous to S. pombe, or P3 secretion signal (34th amino acid residue), and is preferably a secretion signal peptide of S. pombe PDI1.

The secretory carrier protein which functions in S. pombe is preferably a PDI1 full-length protein containing a secretion signal peptide, a PDI1 partial protein, or a protein having such a modified protein fused. Particularly preferred is a protein containing a-domain of PDI1 or a protein containing a'-protein of PDI1, more preferably a protein containing at least one of a-domain and a'-domain and at least one of b-domain and b'-domain of PDI1, further preferably a protein containing at least one of a-domain and a'-domain, at least one of b-domain and b'-domain and x-domain of PDI1 (see Patent Document 3). All the respective domains of PDI1 contained in the protein fused downstream the secretion signal peptide may be derived from a single species, or they may be a combination of domains derived from two or more species.

In the transformant of the present invention, in order for more increased TF secretory production capability, the secretory carrier protein is preferably a fused gene having, in order from the upstream side, a secretion signal peptide gene of S. pombe PDI1 and a gene encoding abx-domain portion of human PDI1 or a gene encoding abb'x-domain portion of human PDI1 directly or indirectly linked, or a fusion protein having a secretion signal peptide gene of S. pombe PDI1, a gene encoding ab-domain portion of human PDI1 or a gene encoding abb'-domain portion of human PDI1, and a gene encoding x-domain portion of S. pombe PDI1 directly or indirectly linked.

TF gene is exogenous to S. pombe. Accordingly, the transformant of the present invention is obtained by biogenetically introducing a TF gene derived from an organism other than S. pombe, into S. pombe. The nucleotide sequence of the TF gene which the transformant of the present invention has may be the gene sequence of the species from which the TF protein is derived as it is, or the gene sequence may be modified by changing its codons to ones frequently used in S. pombe.

The copy number of a gene having the secretion signal peptide gene and the TF gene directly or indirectly linked to each other of the transformant (hereinafter referred to as SP-TF gene) may be one or two or more. The SP-TF gene may be introduced as the plasmid as an extrachromosomal gene in S. pombe, or may be introduced into the plasmid of S. pombe. By introducing a foreign gene to the chromosome, a transformant excellent in the passage stability can be obtained.

Regarding the gene recombination method using yeast as a host, for more stably and efficiently expressing heterologous proteins, various expression systems, particularly an expression vector, a secretion signal, a gene introduction expression vector, etc. are developed, and for production of the transformant of the present invention, they are widely applicable. For example, as an expression system using S. pombe as a host, Japanese Patent No. 2776085, JP-A-H07-163373, JP-A-H10-215867, JP-A-H10-215867, JP-A-H11-192094, JP-A-H11-192094, JP-A-2000-262284, WO96/023890 etc. have been known, and for production of the transformant of the present invention, such expression systems are widely applicable.

Introduction of the SP-TF gene into S. pombe as a host is carried out, for example, by introducing an expression cassette containing the SP-TF gene, and a promoter and a terminate which function in S. pombe as it is into the host cell, or by introducing a vector having such a cassette integrated into the host cell. The expression cassette may contain at least one of a 5'-untranslation region and a 3'-untranslation region, and may contain an auxotrophic complementation marker such as ura4 gene.

As the promoter which functions in S. pombe, a promoter endogenous to S. pombe, such as an alcohol dehydrogenase gene promoter, a nmt1 gene promoter, a fructose 1,6-bisphosphatase gene promoter, an invertase gene promoter (WO99/23223) or a heat shock protein gene promoter (WO2007/26617, WO2014/030644), or a promoter derived from an animal cell virus such as a hCMV promoter or a SV40 promoter may, for example, be mentioned. As the terminator which functions in S. pombe, a LPI (human lipocortin I) terminator may, for example, be mentioned.

As the vector into which the expression cassette is integrated, a plasmid derived from E. coil such as pBR322, pBR325, pUC118, pUC119, pUC18, pUC19 or the like may suitably be used. The vector preferably has a marker to select the transformant. Such a marker may, for example, be ura4 gene (an auxotrophic complementation marker) or isopropyl malate dehydrogenase gene (leu1 gene).

In a case where an expression cassette containing the SP-TF gene is integrated into S. pombe chromosome by a homologous recombination method, the target site into which the expression cassette is integrated may be present in only one position of the S. pombe chromosome, or may be present in two or more positions. In a case where two or more target sites are present, the vector may be integrated into two or more positions in the S. pombe chromosome. When the expression cassette is integrated into one target site, the target site disclosed in JP-A-2000-262284 may, for example, be used. By using two or more types of vectors having different recombination regions, the vectors can be integrated into different target sites.

As the vector having an expression cassette containing the SP-TF gene integrated, a vector having a secretion signal peptide gene and a hTF gene integrated, disclosed in Patent Document 1, Patent Document 3 or the like may, for example, be used.

In the transformant of the present invention, gas2 gene (SPBC29A10.08.1) endogenous to S. pombe as a host is deleted or inactivated. As shown in the following Examples, when a transformant of S. pombe having the SP-TF gene introduced is cultured at high density at a cell-density (optical density measured by a turbidimeter at 660 nm:

$OD_{660}$) of at least 100, the expression amount of Gas2 (1,3-β-glucanosyl transferase) protein, as well as TF, increases. Gas2 protein is a glycoprotein localizing in the cell wall and involved in the biosynthesis of the cell wall of fission yeast, and is not considered to be directly involved in expression and secretion of TF. Nevertheless, in the high density cell culture process of TF expression strain (transformant having the SP-TF gene introduced), Gas2 protein as well as TF protein is secreted in a large amount into the liquid medium, and TF production efficiency decreases. Strangely, the increase of the expression and secretion amount of Gas protein observed at the time of high density culture of TF expression strain is not clearly observed at the time of common batch culture at $OD_{660}$ of from 20 to 30. Since gas2 gene is deleted or inactivated in the transformant of the present invention. Gas2 protein is not expressed and the secretion amount of IF into the liquid medium increases, even at the time of the high density culture.

Further, the entire nucleotide sequence of the *S. pombe* chromosomes is stored and opened to the public in "*Schizosaccharomyces pombe* Gene DB (http://www.genedb.org/genedb/pombe/)" of Sanger Institute. The sequence data of *S. pombe* genes described in the present specification are available from the data base by searching with a gene name or a systematic name.

The transformant of the present invention is preferably one in which at least one type of protease gene (gene encoding protease) is deleted or inactivated. When the protease activity of at least one type of protease gene endogenous to *S. pombe* is deleted or inactivated in the transformant, IF protein production efficiency increases, and TF protein production amount more increases. The transformant of the present invention is preferably one in which at least one type of gene selected from the group consisting of a serine protease gene group (a group of genes encoding serine protease), an amino peptidase gene group (a group of genes encoding amino peptidase), a carboxypeptidase gene group (a group of genes encoding carboxypeptidase), and a dipeptidase gene group (a group of genes encoding dipeptidase) is deleted or inactivated.

The transformant of the present invention may be one in which only one type of protease gene is deleted or inactivated, or may be one in which two or more types of protease gene are deleted or inactivated. Among them, preferred is a transformant in which at least one type of gene selected from the group consisting of a metalloproteinase gene group (a group of genes encoding metalloproteinase), a serine protease gene group, a cysteine protease gene group (a group of genes encoding cysteine protease) and an aspartic protease gene group (a group of genes encoding aspartic protease) is deleted or inactivated, and also preferred is a transformant in which at least one type of gene selected from the group consisting of a metalloproteinase gene group and a serine protease gene group and at least one type of gene selected from the group consisting of a cysteine protease gene group and an aspartic protease gene group, are deleted or inactivated.

The four types of protease gene group of *S. pombe* may, for example, be as follows.

Metalloproteinase gene group: cdb4(SPAC23H4.09), mas2(SPBC18E5.12c), pgp1(SPCC1259.10), ppp20 (SPAC4F10.02), ppp22(SPBC14C8.03), ppp51 (SPAC22G7.01c), ppp52(SPBC18A7.01), ppp53 (SPAP14E8.04).

Serine protease gene group: isp6(SPAC4A8.04), ppp16 (SPBC1711.12), psp3(SPAC1006.01), sxa2 (SPAC1296.03c).

Cysteine protease gene group: ppp80(SPAC19B12.08), pca1(SPCC1840.04), cut1(SPCC5E4.04), gpi8 (SPCC11E10.02c).

Aspartic protease gene group: sxa1(SPAC26A3.01), yps1 (SPCC1795.09), ppp81(SPAC25B8.17).

The transformant of the present invention may be produced by deleting or inactivating gas2 gene of the transformant having an expression cassette containing the SP-TF gene introduced into *S. pombe* as a host, and may also be produced by introducing an expression cassette containing the SP-TF gene into *S. pombe* having gas2 gene preliminarily deleted or inactivated. By using as a host a *S. pombe* mutant strain in which at least one type of protease gene is deleted or inactivated, a transformant into which the SP-TF gene is introduced, in which gas2 gene is deleted or inactivated, and in which at least one type of protease gene is deleted or inactivated, is obtained. The mutant strain in which at least one type of protease gene endogenous to *S. pombe* is deleted or inactivated may, for example, be preferably a *S. pombe* mutant strain in which psp3 gene, isp6 gene, ppp53 gene, ppp16 gene, ppp22 gene, sxa2 gene, ppp80 gene and ppp20 gene are deleted or inactivated, such as A8 strain as disclosed in Patent Document 2.

Deletion or inactivation of gas2 gene, and deletion or inactivation of protease gene may be carried out by publicly known methods. Specifically, the Latour system (Nucleic Acids Res. (2006) 34: ell, and WO2007/063919) can be used to delete the gene. Further, the gene may be inactivated by introducing mutation into a part of the gene by a mutant screening method using mutagens (Koubo Bunshi Idengaku Jikken-Hou, 1996, Japan Scientific Societies Press), random mutations using PCR (PCR Methods Application, 1992, vol. 2, p. 28-33) and the like. Further, the portion at which a specific gene is deleted or inactivated may be an ORF (open reading frame) portion or may be an expression control sequence. Particularly preferred is deletion or inactivation by substituting the ORF portion of structural gene by a marker gene by means of PCR-mediated homologous recombination (Yeast, vol. 15, pages 943 to 951, 1998).

As the transformation method, any known transformation method may be used. The transformation method may, for example, be a conventional method like lithium acetate method, electroporation method, spheroplast method, glass-beads method or the like, and a method disclosed in JP-A-2005-198612. Further, a commercially available yeast transformation kit may be used.

The transformant of the present invention may be cultivated in the same manner as a natural yeast of the genus *Schizosaccharomyces*.

As a liquid medium for culturing the transformant, a known yeast culture medium may be used so long as it contains a carbon source, a nitrogen source, an inorganic salt, etc. which a yeast of the genus *Schizosaccharomyces* can utilizes, and is capable of efficiently culturing a yeast of the genus *Schizosaccharomyces*. The liquid medium may be a natural medium or a synthetic medium.

The liquid medium may, for example, be MMA (Minimal medium with agar), SDC (Synthetic dextrose complete medium), TES (0.5% Bacto-yeast extract, 3% glucose, supplemented with uracil, leucine, histidine, lysine, adenine) or YES (0.5% Bacto-yeast extract, 3% glucose, supplemented with uracil, leucine, histidine, lysine, adenine), or YPD (1% Bacto-yeast extract, 2% Bactopeptone, 2% glucose).

The carbon source may, for example, be a sugar such as glucose, fructose or sucrose. The nitrogen source may, for example, be an inorganic acid or an ammonium salt of an inorganic acid, such as ammonia, ammonium chloride or ammonium acetate, peptone or casamino acid. The inorganic salt may, for example, be magnesium phosphate, magnesium sulfate or sodium chloride. Specifically, a nutrient medium such as YPD medium (M. D. Rose et al.,"Methods In Yeast Genetics", Cold Spring Harbor Labolatory Press (1990)), a minimal medium such as MB medium (K. Okazaki et al., Nucleic AcidsRes., 18, 6485-6489 (1990)) and the like may be used.

Cultivation may be carried out by using a publicly known cultivation method for yeasts such as a shaking cultivation, a stirring cultivation.

The cultivation temperature is preferably from 23 to 37° C., more preferably from 30 to 32° C. Further, the cultivation time may be set appropriately.

Cultivation may be carried out by batch culture or continuous culture.

[Method for Producing TF]

By culturing a transformant (TF expression strain) using S. pombe as a host and having SP-TF gene in a liquid medium, TF protein secreted into the liquid medium after culture can be obtained. As the liquid medium for culturing the TF expression strain and the culture method, a publicly known yeast culture medium may be used and a publicly known culture method may be employed, in the same manner as the culture of the transformant of the present invention.

TF protein is easily decomposed under an acidic condition. Accordingly, in production of TF, the pH of the liquid medium for the culture of the TF expression strain is preferably at least 5.5, more preferably from 5.5 to 6.5. The longer the culture time, the more the pH of the culture broth tends to decrease, and accordingly the pH is properly adjusted so that the pH of the culture broth is maintained to be within a range of from 5.5 to 6.5 at the time of the culture for TF production.

In order to further increase the TF protein secretory production amount, the culture time for culturing the TF expression strain is preferably at least 2 days, more preferably from 3 to 6 days, further preferably from 3 to 5 days.

The liquid medium for culturing the TF expression strain preferably contains adenine. In a case where the TF expression strain has the SP-TF gene with a copy number of at least one, lysis is likely to occur, and the TF expression amount tends to decrease. By culture in an adenine-containing liquid medium, even a TF expression strain having the SP-TF gene with a copy number of at least one favorably grows, thus increasing the TF secretory production efficiency. The adenine content in the liquid medium is, for example, from 0.5 to 200 mg/L, preferably from 1 to 100 mg/L per $OD_{660}$ indicating the cell-density.

Further, in order to improve the TF productivity, the TF expression strain is preferably cultured at high density. It is particularly preferred to conduct fed-batch culture using an initial culture medium at a pH of from 5.5 to 6.5, preferably from 5.5 to 6.0 while the aeration rate into a culture tank, the stirring rate and the feeding rate of the feed medium are controlled. Since the medium is continuously added (fed) in accordance with the growth rate and the nutrition consumption rate while the glucose concentration in the medium is kept low at a certain level, the cell-density improves finally several tens times as compared with batch culture in a test tube or in a flask, a high cell-density is achieved, and a larger amount of TF can be produced by secretion. By high concentration culture of the TF expression strain, culture is conducted preferably until $OD_{660}$ reaches 100 or higher, preferably $OD_{660}$ reaches 200 to 800.

The TF expression strain is preferably the transformant of the present invention. In the transformant of the present invention, Gas2 protein derived from the host is not expressed, and the TF secretory production efficiency is high. In addition, at the time of purification of TF protein from the liquid medium after the high density culture, purification by isolation from Gas2 protein is not necessary, and purification can be carried out more easily.

TF protein can be obtained from the liquid medium after culture by a publicly known method. For example, cells are separated and removed from the liquid medium after culture by centrifugal separation, and the obtained culture supernatant is adsorbed e.g. in an affinity column, followed by washing and elution; impurities such as a dye are removed by activated carbon; or separation may be carried out by using a separation membrane. In a case where the TF expression strain having gas2 gene is cultured at high density, since the recovered culture supernatant contains Gas2 protein in a large amount, after the culture supernatant is subjected to anion exchange chromatography using a DEAE resin, Gas2 protein is inevitably contained in a fraction containing TF protein. Accordingly, TF protein can be separated and purified from Gas2 protein only after the fraction containing TF protein is subjected to hydrophobic interaction chromatography or gel permeation chromatography. Whereas from the culture supernatant after the high density culture of the transformant of the present invention, TF protein can be purified only by subjecting the culture supernatant to anion exchange chromatography using a DEAE resin once.

EXAMPLES

Now, the present invention will be described in further detail with reference to Examples of the present invention and Comparative Examples. However, it should be understood that the present invention is by no means restricted to the following description. In the following Examples, "%" means "mass%" unless otherwise specified.

Example 1

<Preparation of hTF Mutant Gene>

A natural hTF gene ORF (SEQ ID NO:1) encodes a protein with a full-length of 698 residues, having hTF protein fused to a downstream side of secretion signal peptide having 19 residues. By using human cDNA library as a template, PCR was carried out with a primary pair (forward primer No. 9220 (SEQ ID NO:3) and reverse primer No. 9221(SEQ ID NO:4)) to obtain a DNA fragment having restriction enzyme site Af/II and a nucleotide sequence encoding 4 residues (Leu-Lys-Lys-Arg) (SEQ ID NO: 25) of the C-terminal portion of human PDI1 abx-domain at the 5' end of a gene encoding hTF protein, and restriction enzyme site XbaI respectively added at the 3' end, respectively.

A double digestion product with Af/II and XbaI of the DNA fragment obtained was integrated by ligation with a double digestion product with AN and XbaI of pSL6P3 (Patent Document 3) which is a chromosome single-locus integration type secretory expression vector of fission yeast having a gene encoding P3 secretion signal peptide downstream hCMV promoter, and having a multiple cloning site between the gene and LPI terminator, to transform E. coil DH5α to prepare plasmid DNA of expression vector pSL6P3-hTF having a gene encoding natural hTF protein containing 4 residues of the C-terminal portion of abx-domain at the N-terminal cloned.

From a secretory expression vector having an expression cassette of the desired protein integrated into the multiple cloning site of pSL6P3 vector, one copy of a linearized vector fragment cleaved by restriction enzyme NotI, is integrated between adjacent two gene loci leu1-32 and top2 on the fission yeast chromosome, by chromosome homologous recombination. Further, into pSL6P3 vector, a leucine marker gene fragment (leu1$^+$) to complement point mutation (leu1-32) portion of mutant (leu1$^-$) gene (a gene having leucine synthesis gene (leu1) inactivated by point mutation (leu1-32)) is integrated. Accordingly, in a case where a leucine-auxotrophic yeast containing mutant (leu1$^-$) gene is used as a host strain, the transformant having the linearized fragment of pSL6P3 vector integrated with the chromosome is no more auxotrophic for leucine, and the clone can be selected from the minimal medium (MMA plate) containing no leucine.

By PCR method, into the hTF gene in pSL6P3-hTF, a mutation to substitute 413rd and 611st (432nd and 630th of SEQ ID NO:1) aspartic residues of natural hTF protein with glutamic residue was introduced to prepare pSL6P3-hTF (N413Q/N611Q). Specifically, four point mutations to substitute the first nucleotide in the codon encoding each aspartic residue with cytosine (C) and the third nucleotide with adenine (A), were introduced. The sequence of hTF (N413Q/N611Q) having such mutations introduced is shown in SEQ ID NO: 2.

<Preparation of hTF(N413Q/611Q) Expression Vector>

Figure 1:
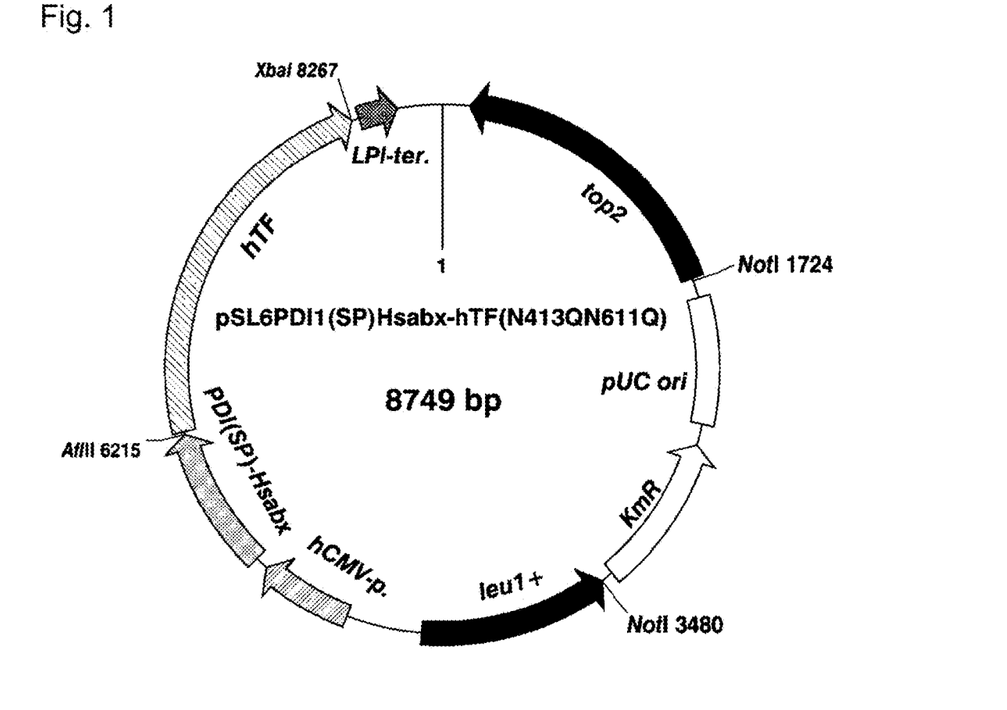
FIG. 1 is a diagram illustrating the structure of secretory expression vector pSL6PDI1(SP)Hsabx-hTF (N413QN611Q).

A DNA fragment containing a region encoding hTF (N413Q/N611Q) having pSL6P3-hTF(N413Q/N611Q) double-digested with AflII and XbaI, was integrated by ligation with a double digestion product with AflII and XbaI of chromosome single-locus integration type secretory expression vector pSL6PDI1(SP)Hsabx-AflII of fission yeast having a gene encoding secretory carrier protein (PDI1(SP)-Hsabx) comprising a secretion signal peptide of S. pombe PDI1, ab-domain of human PDI1 and x-domain of S. pombe PDI1, downstream of hCMV promoter, and having a multiple cloning site between the gene and LPI terminator, to transform E. coli DH5α to prepare pSL6PDI1(SP)Hsabx-hTF(N413QN611Q) (8749 bp, FIG. 1) which is a chromosome single-locus integration type expression vector of a fusion protein of secretory carrier protein (PDI1(SP)-Hsabx) and mutant hTF(N413Q/N611Q) protein.

<Preparation of A8 Strain>

From leucine/uracil-auxotrophic (leu1$^-$ ura4$^-$) ARC010 strain (genotype: h$^-$ leu1-32 ura4-D18) of S. pombe, by Latour method, eight genes i.e. psp3 gene, isp6 gene, ppp53 gene, ppp16 gene, ppp22 gene, sxa2 gene, ppp80 gene and ppp20 gene were deleted to prepare A8 strain (genotype: h$^-$ leu1-32 psp3-D13 isp6-D14 oma1-D10 ppp16-D20 fma2-D13 sxa2-D15 aap1-D17 ppp80-D11). The A8 strain was a leucine-auxotrophic strain. More particularly, by the Latour method, a gene deletion fragment (Latour fragment, comprising homologous recombination regions at both terminals, and ura4$^+$ marker gene and OL (overlapped sequence) region sandwiched between the homologous recombination regions), was once integrated by homologous recombination into the upstream or downstream side of the region to be deleted on the fission yeast genome, to prepare a latent strain. Then, the latent strain was cultured in a medium containing 5'-FOA to cause homologous recombination between OLs integrated, to form a gene deletion strain from which the region to be deleted containing ura4$^+$ marker gene dropped off, as a colony. Deletion of the desired gene from the obtained gene deletion strain was confirmed by PCR. By this method, since no foreign gene containing ura4$^+$ marker gene does not remain, only the desired gene can be deleted without integrating a foreign gene, and in addition, deletion of gene can be carried out repeatedly while the ura4$^+$ marker gene is recycled. The nucleotide sequence of the primer used for preparation of the Latour fragment to delete the genes by PCR is shown in Table 1.

TABLE 1

| Gene | Primer | Nucleotide sequence | SEQ ID NO |
|---|---|---|---|
| psp3 | Forward primer #6164 | GCAAGTACTGCTCTTGATCTG | 5 |
|  | Reverse primer #6167 | TAAAGCATCCACTTTGAGCAA | 6 |
| isp6 | Forward primer #6153 | TCTGTTGGCAACATGTCTC | 7 |
|  | Reverse primer #6156 | GTGAAAGTAGATTATCCATGAGGTC | 8 |
| oma1 | Forward primer #7243 | TGCCTTTTACGGTTCTTTGGTC | 9 |
|  | Reverse primer #7246 | TGCACATCAGGTAGCCCGAC | 10 |
| ppp16 | Forward primer #7255 | TCATTAAGTCGTCGTCAAACGG | 11 |
|  | Reverse primer #7258 | CTTTAGGTCGTCAATTTCGTGC | 12 |
| fma2 | Forward primer #6917 | CATACTCCCCTGATGTTTCGC | 13 |
|  | Reverse primer #6920 | CATTCATGGTGGTAAGAGTGTTCC | 14 |
| sxa2 | Forward primer #9515 | ACCAATCTTCCATATCCCCTTG | 15 |
|  | Reverse primer #9518 | GCTACGAAAGCTTCAACTGCG | 16 |
| aap1 | Forward primer #9883 | ARAGTTCTTTGTTTTCAATTTCCATG | 17 |
|  | Reverse primer #9886 | TCCTTATAAACGAGCTATCGAATTG | 18 |
| atg4 | Forward primer #6175 | GAATCATACTACGATCAGTTGC | 19 |
|  | Reverse primer #6178 | GAAATTTACTCACAGGGAAGAAC | 20 |

<Preparation of A8-Gas2Δ Strain>

From the A8 strain, gas2 gene was deleted by Latour method to prepare A8-gas2Δ strain (genotype: h$^-$ leu1-32 psp3-D13 isp6-D14 oma1-D10 ppp16-D20 fma2-D13 sxa2-D15 aap1-D17 ppp80-D11 gas2-D15). Deletion of the desired gene from the obtained gene deletion strain was confirmed by PCR. The A8-gas2Δ strain was a leucine-auxotrophic strain. The nucleotide sequence of the primer used for preparation of the Latour fragment to delete gas2 gene by PCR is shown in Table 2.

TABLE 2

| Gene | Primer | Nucleotide sequence | SEQ ID NO |
|---|---|---|---|
| gas2 | Forward primer #10493 | GAATGTCCATATAAGTCAATGATGAGC | 21 |
|  | Reverse primer #10496 | GAGGTTAACGACTATGGTCTTGTTAAC | 22 |

The prepared A8 strain and A8-gas2Δ strain were subjected to growth evaluation (measurement of μmax and growth curve) on a test tube scale (under conditions of inoculation to 5 mL of YES and culture at 30° C. for 68 hours). As a result, both the strains were confirmed as follows. Although the maximum relative growth rate (μmax relative value) indicating the initial rising of cell growth slightly decreased (a decrease of about 8 to 12%) as compared with the same auxotrophic (leu1⁻) wild type strain (ARC001), the ultimate cell-density ($OD_{660}$) slightly increased (an increase of about 9 to 17%), and both the strains could grow in the same manner as leucine-auxotrophic wild type strain (not shown). Particularly, no difference in the growth and the phenotype between A8 strain and A8-gas2Δ strain was observed.

<Preparation of hTF(N413Q/N611Q) Gene One Copy Expression Strain> pSL6PDI1(SP)Hsabx-hTF(N413QN611Q) was cleaved by restriction enzyme NotI to prepare a linearized vector fragment (6993 bp), and the vector fragment was integrated by means of lithium acetate method to transform leucine-auxotrophic S. pombe A8 strain of A8-gas2Δ strain as a host. Cells after transformation were applied to a MMA plate, and a colony formed by being made to be leucine-auxotrophic, was obtained as a recombinant clone. Then, a clone which was confirmed by PCR that the desired gene was appropriately introduced, was selected as a positive clone (hTF (N413Q/N611Q) expression strain). Transformants having pSL6PDI1(SP)Hsabx-hTF(N413QN611Q) introduced into A8 strain and A8-gas2Δ were respectively named A8-hTF(1) strain and A8-gas2Δ-hTF(1) strain.

<Secretory Production of hTF(N413Q/N611Q) One Copy Expression Strain>

A8-hTF(1) strain and A8-gas2Δ-hTF(1) strain were cultured to express hTF(N413Q/N611Q) by secretion. Specifically, in 5 mL of YES in a glass test tube, they were subjected to raising culture and pre-culture respectively for 24 hours, and in 5 mL of YPD+MES medium(a liquid medium having 0.3M MES buffer contained in YPD) (pH 6.0) in a glass test tube, shake-cultured at 32° C. for 3 days or 5 days. The cell-density at the completion of culture (ultimate $OD_{660}$) was from 30 to 36. The culture supernatant fraction recovered from the culture broth and the cell pellet were respectively subjected to SDS-PAGE analysis and confirmed that hTF(N413Q/N611Q) were expressed inside and outside the cells (not shown). Further, with respect to both A8-hTF(1) strain and A8-gas2Δ-hTF(1) strain, the hTF(N413Q/N611Q) amount in the cell pellet was larger and the hTF(N413Q/N611Q) amount in the culture supernatant was larger in the one cultured for 5 days than in the one cultured for 3 days. Therefore, it was conformed that by prolonging the culture time, the secretion amount of hTF (N413Q/N611Q) can be increased and the amount remaining in the cells without secretion can be decreased.

<Results of hTF(N413Q/N611Q) One Copy Expression Strain>

A8-gas2Δ-hTF(1) strain was cultured to express hTF (N413Q/N611Q) by secretion. Specifically, in 5 mL of YES in a glass test tube, the strain was subjected to raising culture and pre-culture respectively for 24 hours, and then using a 24-well plate, shake-cultured in 5 mL of an adenine-containing YPD+MES medium (pH 6.0) at 32° C. for 3 days, 4 days or 5 days, and subjected to ELISA using a commercial kit (tradename: "Human Transferrin ELISA Quantitation Set", manufactured by Bethyl Laboratories), and the hTF (N413Q/N611Q) protein amount secreted into the culture supernatant after completion of the culture was measured. The longer the culture time, the larger the hTF(N413Q/N611Q) secretion amount. The secretion amount of hTF (N413Q/N611Q) per culture supernatant over 5 days of culture was from 30 to 40 mg/L in A8-gas2Δ-hTF(1) strain.

<High Density Culture of hTF(N413Q/N611Q) One Copy Expression Strain>

A8-hTF(1) strain and A8-gas2Δ-hTF(1) strain were cultured at high density to express hTF(N413Q/N611Q) by secretion. Specifically, on a 5L culture scale, fed-batch culture was conducted using an initial culture medium at a pH of the culture broth of from 5.5 to 6.0 while the aeration rate into a culture tank, the stirring rate and the feeding rate of the feed medium were controlled. As the liquid medium, an adenine-containing semisynthetic medium (several % Bacto-yeast extract, synthetic components such as glucose, vitamins, minerals, inorganic salts, etc.) was used. The medium was continuously added (fed) in accordance with the growth rate and the nutrition consumption rate, while the glucose concentration was kept low at 2%. Finally, the cell-density ($OD_{660}$) reached a level of from 200 to 800.

Figure 2:
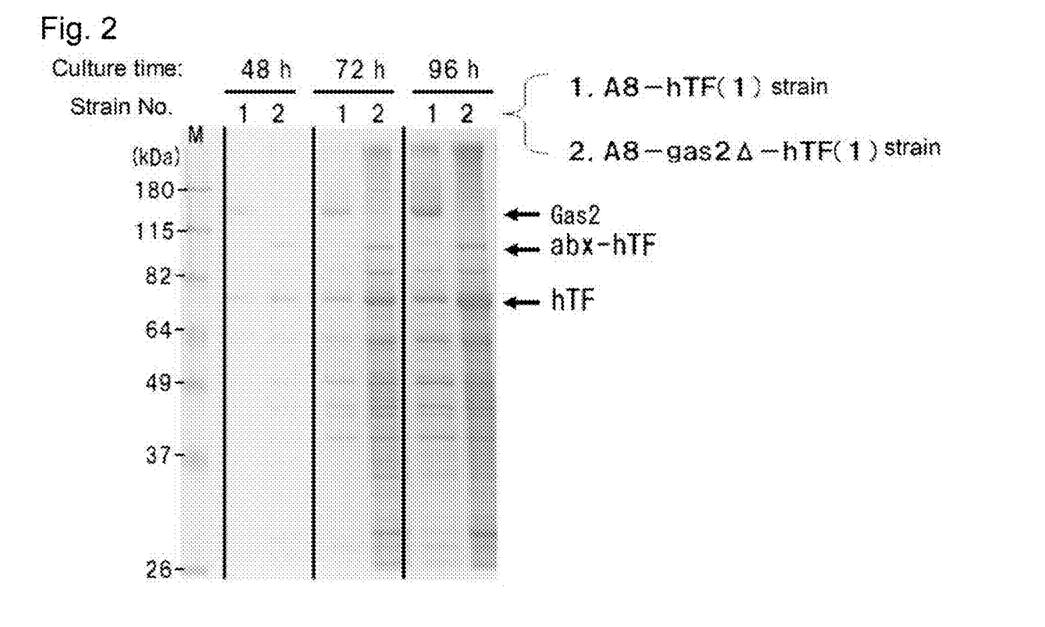
FIG. 2 is a CBB stained image of culture broths of A8-hTF(1) strain and A8-gas2Δ-hTF(1) strain after SDS-PAGE.

The culture broth was sampled with time and subjected to SDS-PAGE, and the results are shown in FIG. 2. 5 μL of the culture broth was applied to each lane. In FIG. 2, "hTF" indicates a hTF(N413Q/N611Q) band. As shown in the CBB staining image in FIG. 2, expression of Gas2 was suppressed in A8-gas2Δ-hTF(1) strain, and the secretion amount of hTF(N413Q/N611Q) in A8-gas2Δ-hTF(1) strain was larger than in A8-hTF(1) strain in all the cases of the culture time of 48, 72 and 96 hours.

Figure 3:
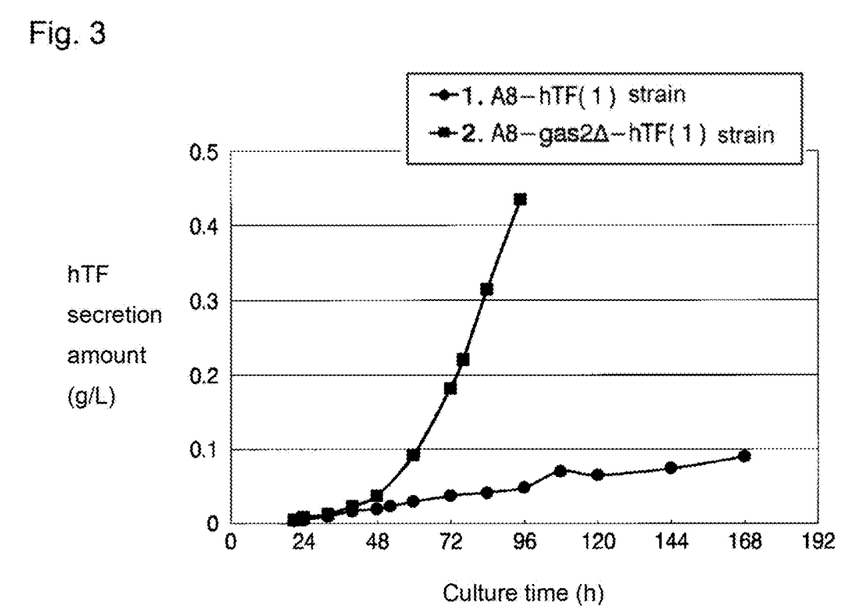
FIG. 3 is a graph illustrating changes with time of the secretion amounts of hTF(N413Q/N611Q) protein from A8-hTF(1) strain and A8-gas2Δ-hTF(1) strain.

Further, ELISA was conducted in the same manner as above using the sampled culture broth, and the hTF(N413Q/N611Q) protein amount secreted into the culture supernatant was measured. As shown in FIG. 3, there was no difference in the secretion amount between the two strains from beginning of the culture up to about 48 hours, however, after about 48 hours, the secretion amount of hTF(N413Q/N611Q) in A8-gas2Δ-hTF(1) strain was definitely larger than in A8-hTF(1) strain. The ultimate secretion amounts of the two strains (secretion amounts 168 hours after beginning of the culture in the case of A8-hTF(1) strain and 96 hours after beginning of the culture in the case of A8-gas2Δ-hTF (1) strain) are shown in Table 3. Of A8-gas2Δ-hTF(1) strain, the hTF secretion amount per culture broth was at least 4.8 times and the hTF secretion amount per cell (per $OD_{660}$) was at least 2.1 times those of A8-hTF(1) strain.

TABLE 3

| hTF expression | hTF secretion amount per culture broth (g/L) | hTF secretion amount per cell (mg/OD660) |
|---|---|---|
| A8-hTF(1) strain | 0.09 | 2.04 |
| A8-gas2Δ-hTF(1) strain | 0.43 | 4.33 |

The cells were removed by centrifugal separation from the culture broth after high density culture, and the recovered culture supernatant was subjected to DEAE chromatography to purify hTF. As the DEAE column, a column packed with a DEAE resin (DEAE Sepharose FF(Fast Flow)) (tradename: "XK26", manufactured by GE Healthcare) was used. Specifically, 900 mL of the culture supernatant was applied to a DEAE column (1 CV=60.6 mL) equilibrated with an equilibration buffer (20 mM Tris-HCl, pH 8.5), and then an elution buffer B (20 mM Tris-HCl, 1M NaCl, pH 8.5) was applied under gradient conditions of from 0% (15 CV) to 100% (5 CV) for elution. The fraction size was 30.3 mL.

Figure 4:
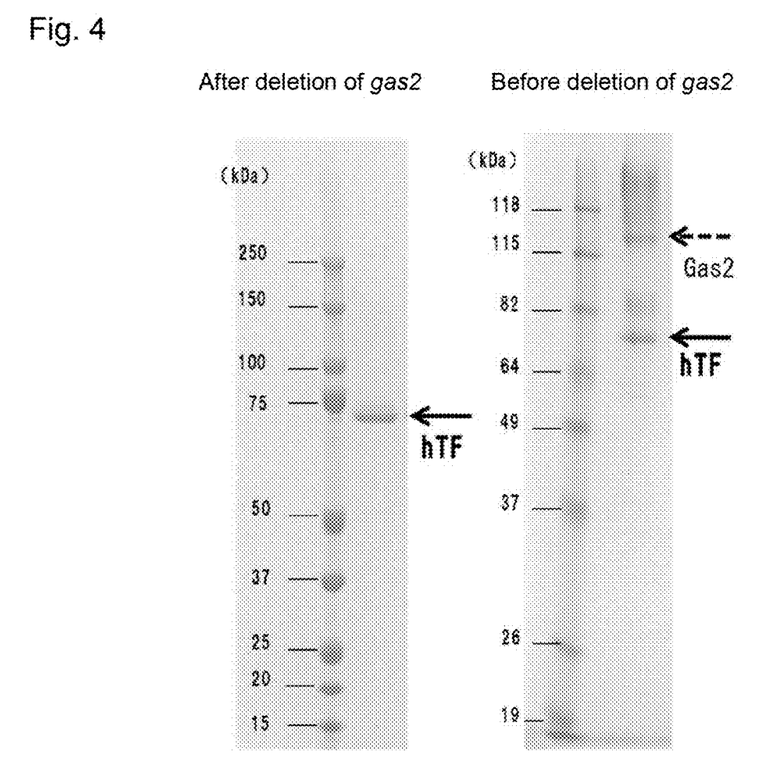
FIG. 4 is CBB stained images of fractions of hTF(N413Q/N611Q) protein in culture supernatants of A8-hTF(1) strain and A8-gas2Δ-hTF(1) strain, purified by DEAE chromatography, after SDS-PAGE.

Fractions containing hTF(N413Q/N611Q) protein (the 3rd to 6th fractions) were recovered together and subjected to SDS-PAGE, and the results are shown in FIG. 4. In FIG. 4, the lane "after deletion of gas2" indicates the CBB staining image of the purified fractions from the culture broth of A8-gas2Δ-hTF(1) strain, and the lane "before deletion of gas2" indicates the CBB staining image of the purified fractions from the culture broth of A8-hTF(1) strain. As shown in the CBB staining images in FIG. 4, in the purified fraction from the culture broth of A8-gas2Δ-hTF(1) strain, only a hTF(N413Q/N611Q) protein band was detected, and it was confirmed that hTF(N413Q/N611Q) protein could be separated from other proteins and purified at high purity only by DEAE chromatography once. Whereas in the purified fraction from the culture broth of A8-hTF(1) strain, in addition to the hTF(N413Q/N611Q) protein band, a plurality of bands were detected at higher molecular weight side. Among them, the band in the vicinity of 115 kDa was taken out and subjected to N terminal sequencing analysis and confirmed to be a Gas2 band. Since secretion of Gas2 was not definitely confirmed by culture at conventional cell-density, it was considered to be characteristic of high density culture. In A8-hTF(1) strain, Gas1 secretory production amount increases in addition to hTF(N413Q/N611Q), which indicates that the hTF(N413Q/N611Q) secretion production amount is kept low as compared with A8-gas2Δ-hTF(1) strain.

What is claimed is:

1. A *schizosaccharomyces pombe* host cell comprising a nucleic acid comprising a nucleotide sequence encoding and capable of expressing a secretion signal peptide and a transferrin protein, wherein the secretion signal peptide is fused to the N-terminus of the transferrin protein, wherein a gas2 gene, endogenous to the host cell, is deleted or inactivated.

2. The host cell according to claim 1, wherein the transferrin protein is a mammalian transferrin protein.

3. The host cell according to claim 2, wherein the mammalian transferrin protein is a human transferrin protein.

4. The host cell according to claim 2, wherein the mammalian transferrin protein is a mutant mammalian transferrin protein in which an aspartic residue capable of having an N-linked glycosylation has been deleted or substituted with another amino acid residue.

5. The host cell according to claim 4, wherein the mutant mammalian transferrin protein is a mutant human transferrin protein in which the aspartic acid residue capable of having an N-linked glycosylation has been deleted or substituted with another amino acid residue.

6. The host cell according to claim 1, wherein at least one protease gene endogenous to the host cell is deleted or inactivated.

7. The host cell according to claim 6, wherein the at least one protease gene is a gene selected from the group consisting of a metalloproteinase gene, a serine protease gene, a cysteine protease gene and an aspartic protease gene.

8. The host cell according to claim 6, wherein the at least one protease gene is a gene selected from the group consisting of psp3gene, isp6 gene, ppp53 gene, ppp16 gene, ppp22 gene, sxa2 gene, ppp80 gene and ppp20 gene.

9. The host cell according to claim 1, wherein the nucleotide sequence encodes and is capable of expressing a secretory carrier protein comprising the secretion signal peptide, which is fused to the N-terminus of the transferrin protein.

10. The host cell according to claim 9, wherein the secretion signal peptide is selected from the group consisting of an *S. pombe*PDI1, a gene encoding an ab-domain portion of human PDI1, and a gene encoding an x-domain portion of *S. pombe* PDI1.

11. The host cell according to claim 1, wherein the secretion signal peptide is fused to the N-terminus of the transferrin protein via a polypeptide linker.

12. A method for producing transferrin, which comprises culturing the host cell of claim 1 in a liquid medium and obtaining transferrin from the liquid medium.

13. The method according to claim 12, wherein the liquid medium has a pH of from 5.5 to 6.5.

14. The method according to claim 12, wherein the liquid medium comprises adenine.

15. The method according to claim 12, wherein the host cell is cultured until the cell-density ($OD_{660}$) reaches 100 or higher, and then transferrin is obtained from the liquid medium.

16. A method for producing the *S. pombe* host cell of claim 1, comprising introducing the nucleic acid comprising the nucleotide sequence encoding and capable of expressing the secretion signal peptide and the transferrin protein, wherein the secretion signal peptide is fused to the N-terminus of the transferrin protein, into an *S. pombe* host cell, and deleting or inactivating the gas2 gene endogenous to the host cell.

* * * * *